United States Patent [19]
Herrmann et al.

[11] Patent Number: 5,542,906
[45] Date of Patent: Aug. 6, 1996

[54] ACOUSTIC THERAPY APPARATUS FOR TREATMENT WITH FOCUSED WAVES

[75] Inventors: Klaus Herrmann, Nuremberg; Guenther Krauss, Erlangen, both of Germany

[73] Assignee: Siemens Aktiengesellschaft, Munich, Germany

[21] Appl. No.: 435,843

[22] Filed: May 5, 1995

Related U.S. Application Data

[63] Continuation of Ser. No. 194,521, Feb. 10, 1994, abandoned.

[30] Foreign Application Priority Data

Mar. 2, 1993 [DE] Germany .................. 43 06 459.0

[51] Int. Cl.$^6$ .................................................. A61B 17/22
[52] U.S. Cl. .................. 601/2; 128/653.1; 601/4
[58] Field of Search ........................ 128/653.1, 660.03, 128/660.01; 601/2, 4

[56] References Cited

U.S. PATENT DOCUMENTS

| | | | |
|---|---|---|---|
| 4,674,505 | 6/1987 | Pauli et al. | 128/328 |
| 4,697,588 | 10/1987 | Reichenberger | 128/328 |
| 4,811,725 | 3/1989 | Grasser | 601/4 |
| 4,914,588 | 4/1990 | Schittenhelm | 601/4 |
| 4,930,509 | 6/1990 | Brisson | 601/4 |
| 4,936,291 | 6/1990 | Forssmann et al. | 128/660.03 |
| 4,971,039 | 11/1990 | Noske et al. | 601/4 |
| 4,984,565 | 1/1991 | Rattner et al. | 128/24 |
| 5,044,354 | 9/1991 | Goldhorn et al. | 601/4 |
| 5,065,761 | 11/1991 | Pell | 601/4 X |
| 5,065,762 | 11/1991 | Ifflaender et al. | 601/4 X |
| 5,070,861 | 12/1991 | Einars et al. | 601/4 |
| 5,230,329 | 7/1993 | Puppo | 601/4 |
| 5,240,000 | 8/1993 | Herrmann et al. | 601/4 |
| 5,285,772 | 2/1994 | Rattner | 601/4 |
| 5,327,890 | 7/1994 | Matura et al. | 601/2 |
| 5,350,351 | 9/1994 | Saffer | 128/653.1 |

FOREIGN PATENT DOCUMENTS 4003350  4/1991  Germany .................. 601/4

Primary Examiner—Krista M. Zele
Assistant Examiner—Brian L. Casler
Attorney, Agent, or Firm—Hill, Steadman & Simpson

[57] ABSTRACT

A therapy apparatus has a source of acoustic waves which generates acoustic waves focused onto a focus and an x-ray locating means with which the subject to be treated can be irradiated from different directions, the central ray of the locating beam assuming a first direction for a first irradiation direction and comprises a second direction for a second irradiation direction. The apparatus has a positioning system with which the subject to be treated and the focus can be adjusted relative to one another. The region to be treated and the focus are adjustable relative to one another by synchronous actuation of the positioning system in two adjustment directions for at least one irradiation direction, this adjustment taking place in a direction that proceeds parallel to the direction of the central ray that belongs to the other irradiation direction.

17 Claims, 5 Drawing Sheets

ACOUSTIC THERAPY APPARATUS FOR TREATMENT WITH FOCUSED WAVES

This is a continuation, of application Ser. No. 08/194,521, filed Feb. 10, 1994 now abandoned.

BACKGROUND OF THE INVENTION

1. Field Of the Invention

The present invention is directed to a therapy apparatus for treatment with focused acoustic waves of the type having a source of acoustic waves which generates acoustic waves focused onto a focus, an x-ray locating system for locating a region to be treated in a subject with which the subject can be transilluminated from different directions, a central ray of the locating beam assuming, in a common plane, a first direction for a first irradiation direction and a second direction for a second irradiation direction, and a positioning device for adjusting the subject and the focus relative to one another, such that the region to be treated is located in the focus of acoustic waves in the way required for the therapy.

2. Description of the Prior Art

Such therapy systems are suitable, for example, for the treatment of stone conditions (lithotripsy), for treating tumors or for treating bone conditions (osteorestoration). In the first instance, a shock wave source is usually provided as the source of acoustic waves. In the case of tumor treatment, for example, a pressure pulse source that generates negative pressure pulses (under-pressure) and/or an ultrasound source that emits continuous ultrasound (hyperthermia) can be provided as the source of acoustic waves. A shockwave source is likewise normally provided as the source of acoustic waves for treating bone conditions.

In therapy systems of the type initially described (see, for example, European Application 0 405 282), the positioning device is normally and adjustment system with which the region to be treated and the focus are adjustable relative to one another in a first adjustment direction that usually perpendicularly intersects the plane containing the central ray of the locating beam. Moreover, the adjustment device usually permits adjustment in a second direction as well as a third adjustment direction, which are selected such that the region to be treated and the focus are adjustable relative to one another in the plane of the central ray. The three adjustment directions thereby usually proceed parallel to the axes of a rectangular (Cartesian) coordinate system.

For positioning a region to be treated in the focus, one usually proceeds by first irradiating the subject to be treated with the x-ray locating means in the first irradiation direction and the region to be treated is brought into the plane of the central ray by movement in the first adjustment direction. By movement in the second adjustment direction, care is subsequently exercised to insure that the region to be treated lies on the central ray proceeding in the first direction. The x-ray locating means is now pivoted and the subject to be treated is irradiated from the second transillumination direction. For adjustment in the third adjustment direction, which proceeds parallel to the first direction assumed by the central ray in the first irradiation direction, care is exercised to insure that the region to be treated comes to lie on the central ray proceeding in the second direction. When this is the case, the region to be treated is located in that point through which the central ray proceeds in the first direction as well as in the second direction, and in which the focus of the acoustic waves is also located. The treatment can then be begun.

It can be expedient for various reasons, for example, anatomical reasons, to select the first and second irradiation directions such that neither of the second nor the third adjustment directions proceeds parallel to the first direction or to the second direction of the central ray. When this is the case, it is not possible to bring the region to be treated into the focus in the above-described way on the basis of a single adjustment in the third adjustment direction. This can only be accomplished in an iterative sequence on the basis of repeated changing between the first and second irradiation directions. This is an undesirable condition in clinical practice since, first, the subject to be treated is exposed to an unnecessarily high radiation dose and, second, the locating event becomes extremely complicated.

SUMMARY OF THE INVENTION

An object of the present invention is to provide a therapy apparatus of the type initially described which permits a rapid implementation of the locating event that is gentle on the patient, even when none of the adjustment directions of the adjustment system coincides with the first or with the second direction of the central ray of the locating system.

This object is in a therapy apparatus for treatment with focused acoustic waves constructed in accordance with the principles of the present invention including a source of acoustic waves which generates acoustic waves focused onto a focus, an x-ray locating means for locating a region to be treated in a subject with which the subject can be irradiated from different directions, whereby its central ray assuming a first direction for a first irradiation direction and a second direction for a second irradiation direction and lying in a common plane for both irradiation directions, and a positioning device for adjusting the subject and the focus relative to one another which includes adjustment means with which the region to be treated and the focus are adjustable relative to one another in a first adjustment direction intersecting the aforementioned plane, and are adjustable relative to one another in this plane in a second direction as well as in a third adjustment. The adjustment means can be actuated and driven synchronously in the second and in the third adjustment directions such that a relative motion between the region to be treated and the focus occurs for at least one irradiation direction, the direction of this relative motion proceeding parallel to the direction of the central ray for the other irradiation direction.

As a consequence of the synchronous actuation of the adjustment means in the second and third adjustment directions, a relative motion between the region to be treated and the focus is produced in the therapy apparatus of the invention which, for at least one irradiation direction, proceeds in a direction parallel to the direction of the central ray for the other irradiation direction. Despite the fact that none of the adjustment directions coincides with the first or second directions of the central ray, a simple locating that is gentle on the patient is assured. Additionally, the advantage is achieved that the positioning device can be formed by a standard support table adjustable in the directions of the three spatial axes, provided with adjustment means which are driven synchronously in the second and third adjustment directions as described above.

It is theoretically possible to simultaneously actuate the adjustment means for a plurality of adjustment directions in the apparatus disclosed in European Application 0 405 282 such that relative motions in several directions are possible. However, there are no means provided to synchronously actuate the adjustment means and, in particular, no means are provided to drive the adjustment means in the second and third adjustment directions such that the relative motion proceeds parallel to a irradiation direction.

If a relative motion between the region to be treated and the focus is possible for only one irradiation direction, proceeding parallel to the direction of the central ray of the other irradiation direction, one must necessarily proceed such that the subject to be treated is first irradiated in this latter irradiation direction for the purpose of locating, since otherwise a proper positioning of the region to be treated in the focus would not be achieved with only two irradiations. In order to permit the locating sequence to begin with one of the two irradiation directions as desired in accord with the anatomical requirements of the respective therapy, in a preferred embodiment of the invention the adjustment means for the first and for the second irradiation directions are actuatable synchronously in the second and third adjustment directions such that a relative motion between the region to be treated and the focus occurs, the direction of the relative motion proceeding parallel to the second direction of the central ray for the first irradiation direction and proceeding parallel to the first direction of the central ray for the second irradiation direction. In this way, it is always assured that a positioning of the region to be treated in the focus is possible with two irradiations.

In further embodiments of the invention the x-ray locating means and the acoustic source are adjustable in common in the first and second adjustment directions, and the patient support is adjustable in the third adjustment direction, which is preferably the vertical direction. A structurally simple and consequently economic structure of the therapy apparatus is achieved as a result. Making the patient support vertically adjustable makes it possible to lower the patient support to an extent, on the basis of an apparatus movement that is required anyway, such that a patient can be placed on the support without particular exertions on the part of the attending personnel, or the patient can easily get on the support unassisted. In order to preclude the source of acoustic waves from presenting an impediment to such activity, the source of acoustic waves is adjustable into a standby position wherein it is located outside the beam path of the x-ray locating means.

In order to be able to achieve a compact structure of the therapy apparatus, the components are arranged so that a plane which contains the central ray both in the first and second directions proceeds essentially at a right angle relative to the longitudinal axis of the patient support. In a further version of the invention, the x-ray locating means is mounted so as to be pivotable around an axis proceeding substantially parallel to the longitudinal axis of the patient support. This can be realized in a technologically simple way by attaching the x-ray locating means to a C-arm that is pivotable around its center axis, which preferably coincides with the longitudinal axis of the support table, and which preferably proceeds through an isocenter. The central ray of the x-ray locating means also preferably proceeds through this isocenter for both irradiation directions.

DESCRIPTION OF THE PREFERRED EMBODIMENTS

Figure 1:
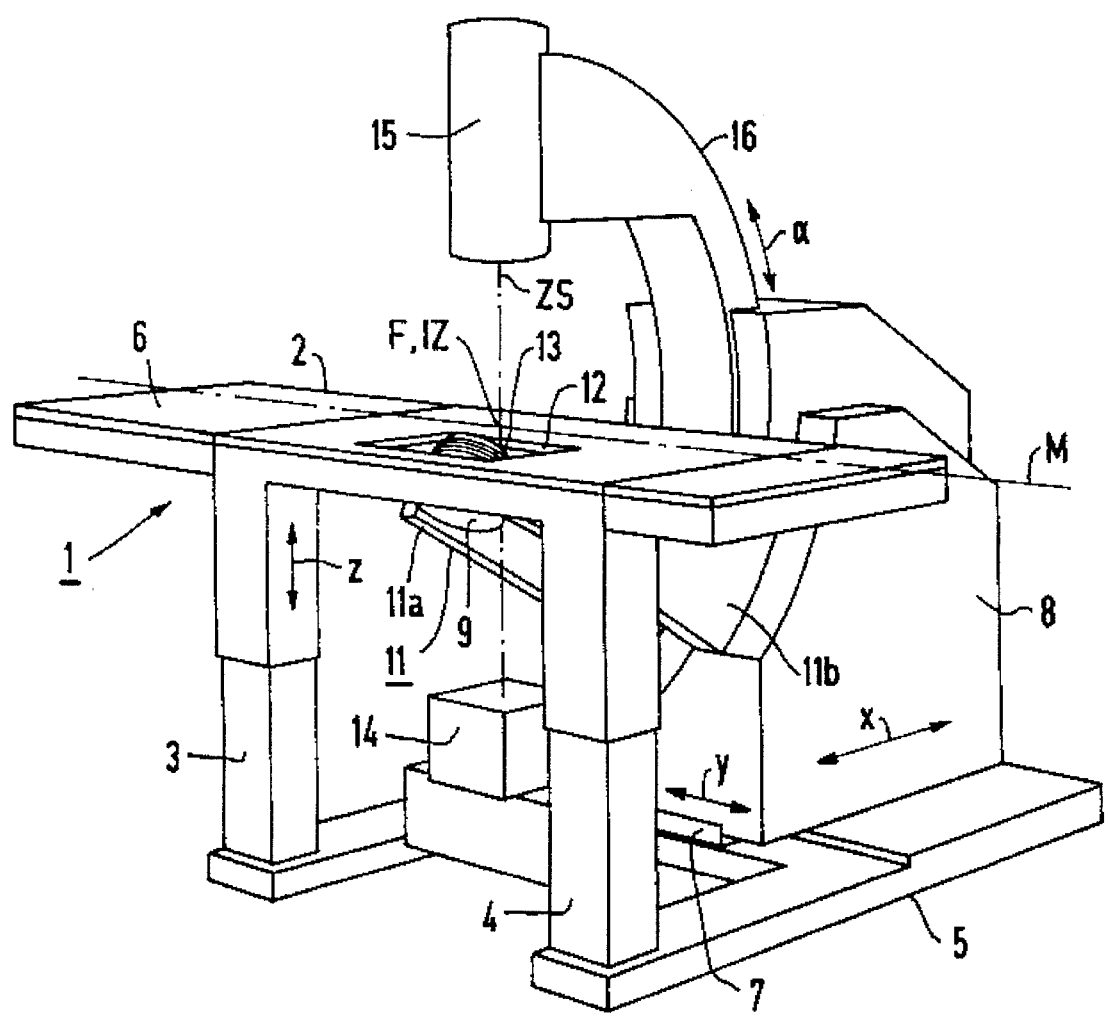
FIG. 1 is a perspective view of a lithotripsy work station constructed in accordance with the principles of the present invention.

As shown in FIG. 1, the therapy apparatus of the invention has a support table generally referenced 1, for a subject to be treated. The bed plate 2 of the support table 1 being height-adjustable with reference to a base 5 by means of two telescoping columns 3 and 4. The bed plate 2 has a preferably horizontal upper side forming the bearing surface 6 for a patient to be treated. The bed plate is height-adjustable in the direction of the double arrow z, and thus parallel to the z-axis of the spatial coordinate system entered in FIG. 1 in a known manner.

A carriage 7 is seated on the base 5 adjustable on a straight line in the direction of the longitudinal axis of the bed plate 2, which proceeds parallel to the y-axis of the spatial coordinate system, as indicated by the double arrow y. A carrier generally referenced 8 is seated on the carriage 7 so as to be longitudinally displaceable in a direction that proceeds transversely relative to the longitudinal axis of the bed plate 2 and thus parallel to the x-axis of the spatial coordinate system, as indicated by the double arrow x.

The bearing of the carriage 7 on the base 5, and the bearing of the carrier 8 on the carriage 7 ensues with known longitudinal guides (not shown), which can be rolling bearings or plain bearings.

The carrier 8 is thus adjustable relative to the bed plate 2 in a plane proceeding parallel to the bearing surface 6, and the bed plate 2 is adjustable relative to the carrier 8 in a direction that proceeds at a right angle to this plane. The adjustment of the carrier 8, the carriage 7 and the bed plate 2 in the direction of the double arrows x, y, z ensues by motor drive with suitable motors (not shown), such as electric motors, and suitable mechanical gearings as required.

The therapy apparatus also includes a source 9 of focused acoustic waves which, for example, may be an electromagnetic shockwave source of the type disclosed in European Application 0 372 119. The source 9 thus has a central x-ray-transparent region formed by an opening 10 (see FIGS. 2 and 3) and through which the acoustic axis A of the source 9 proceeds. The focus of the acoustic waves generated by the source 9 lies on this acoustic axis A. Further details with respect to electromagnetic shockwaves sources are described in U.S. Pat. No. 4,674,505 and European Application 0 188 750, their disclosure being incorporated herein by reference.

Figure 2:
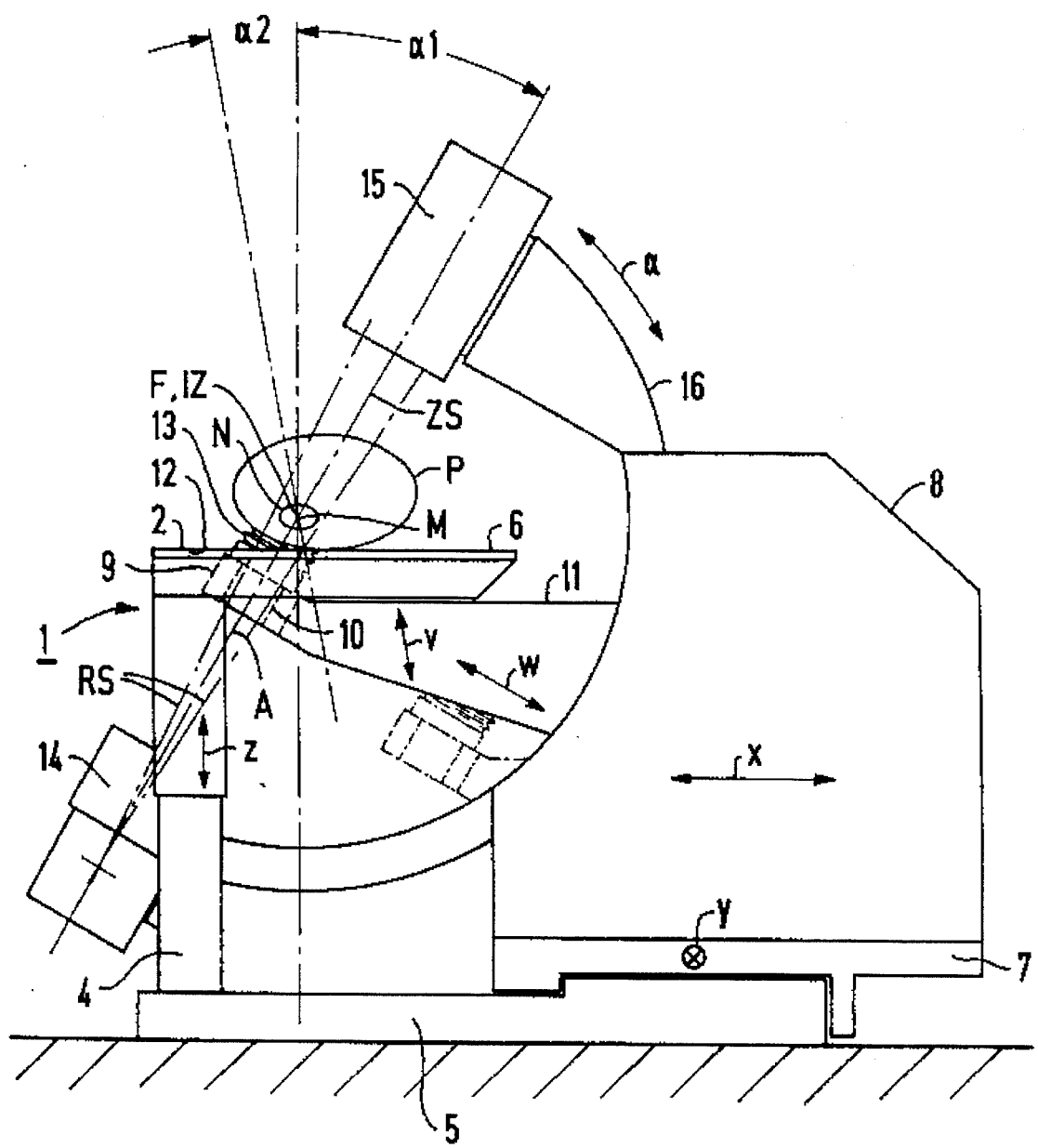
FIGS. 2 and 3 respectively show front views of the lithotripsy work station according to FIG. 1 in different operating conditions.

The source 9 is attached to a source carrier 11, which is in turn attached so as to be longitudinally displaceable relative to the carrier 8 such that the source 9—proceeding from a standby position indicated with broken lines in FIG. 2—can be adjusted on a straight line in the direction of the double arrow w into its working position shown in FIG. 1 (that is shown with solid lines in FIG. 2).

When the source 9 assumes its working position, the focus F is located in an isocenter IZ above the bearing surface 6 of the bed plate 2. The acoustic axis A of the source 9 then proceeds through the isocenter IZ. In its working position, moreover, the source 9 a bellows-like its flexible coupling cushion 13 which projects through an opening 12 of the bed plate 2. The coupling cushion 13 forms the coupling means required for acoustic coupling to a subject to be treated.

An x-ray locating means which includes an oppositely-disposed x-ray radiator 14 and x-ray image intensifier 15, and is also attached to the carrying part 8. These components are attached to the ends of an arcuately curved C-arm 16. The C-arm 16 is mounted at its circumference so as to be adjustable in the direction of the curved double arrow α so that the C-arm 16 can be pivoted around its center axis M. The central ray ZS of the x-ray beam of the x-ray locating means, whose edge rays RS are shown in FIG. 2, intersects the center axis M of the C-arm at a right angle. The C-arm 16 is also attached to the carrier 8 such that the center axis M of the C-arm 16 and the central ray ZS proceed through the isocenter IZ. It is thus assured that the central ray ZS of the x-ray locating means proceeds through the isocenter IZ for any desired pivot position of the C-arm 16. The source 9, moreover, is attached to the source carrier 11 such that the acoustic axis A and the central ray ZS lie in a common plane when the source 9 assumes its working position. In the case of this exemplary embodiment, the adjustment motion of the source 9 from its standby position into its working position and vice versa ensues such that the acoustic axis A and the central ray ZS always lie in a common plane. The adjustment of the source 9 from its standby position into its working position and vice versa in the direction of the double arrow w, as well as the pivoting of the C-arm 16 in the direction of the double arrow α ensue by motor drive, preferably by means of electric motors and suitable gearings (not shown) as required.

Figure 3:
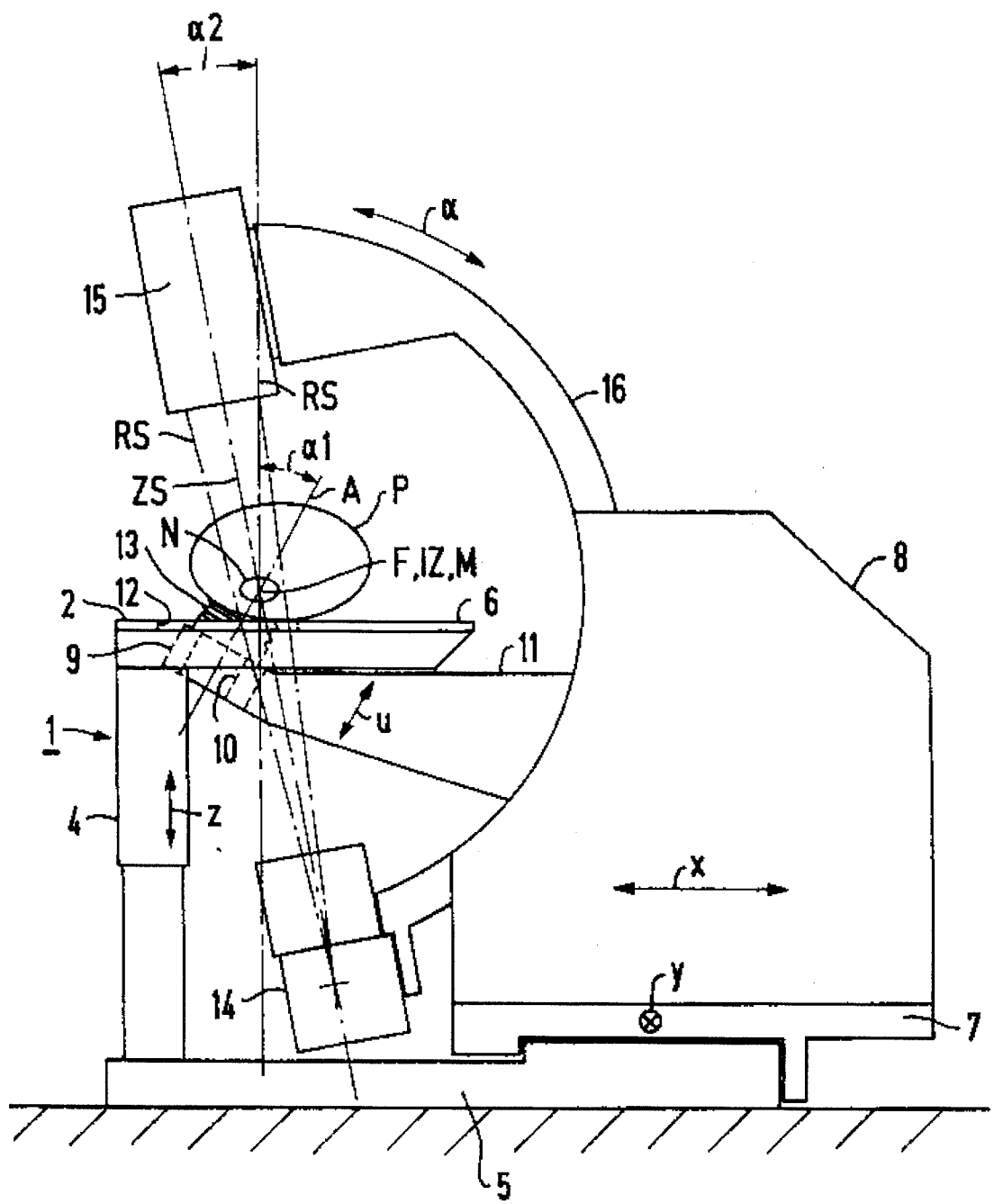

In order to be able to spatially locate a region to be treated, for example a kidney stone in the kidney N of a patient P, with the x-ray locating means and in order to be able to adjust the region into the isocenter IZ, and thus into the focus F of the source 9 in its working position, the patient P (shown schematically in cross-section in FIG. 2), is irradiated in a known way with the x-ray locating means from two different directions. The required information about the spatial position of the kidney stone is thereby obtained. The position of the x-ray locating means and of the source 9 relative to one another corresponding to the first irradiation direction is shown in FIG. 2. In accord therewith, the C-arm 16 assumes a position for the first irradiation direction wherein the central ray ZS proceeds in a first direction and intersects the vertical at an angle α1 of, for example, +30°. In this position, the central ray ZS of the x-ray locating means and the acoustic axis A of the source 9 in its working position coincide. Consequently, the useful x-ray beam proceeds through the x-ray-transparent region of the source 9 formed by the opening 10. The position of the x-ray locating means and the source 9 relative to one another corresponding to the second irradiation direction is shown in FIG. 3. In this position, the central ray ZS proceeds in a second direction in which it intersects the vertical at an angle α2 of, for example, −10°. The useful x-ray beam, whose edge rays RS are shown in FIG. 2, proceeds essentially past the source 9 in this position. Only a slight part of the useful x-ray beam is incident on the source 9, so that no serious degradation of the image information available in the first irradiation direction occurs. In its standby position the source 9 is situated entirely outside the useful x-ray beam.

For reasons described below, the drives for the height adjustment of the bed plate 2 in the direction of the z-axis and for the adjustment of the carrier 8 in the direction of the x-axis are synchronized in the first and second irradiation directions. These drives are synchronized so that the two drives are only actuatable in common, at least during a fine locating event described below. For the first irradiation direction, the resultant motion of the region to be treated and the isocenter IZ relative to one another is parallel to the direction of the central ray ZS in the second irradiation direction. For the second irradiation direction, this resultant motion is parallel to the direction of the central ray ZS in the first irradiation direction. The directions of these relative motions are indicated in FIGS. 2 and 3 with double arrows respectively referenced v and u. This is achieved by selecting the respective adjustment speeds in the x-direction and z-direction are such that the quotient of the speed in x-direction and the speed in z-direction is equal to tan α2 for the first irradiation direction and is equal to tan α1 for the second irradiation direction.

For the implementation of a treatment, the source 9 is first brought into its standby position. The patient P then mounts the bed plate 2 or is placed on the bed plate 2 by the attending personnel. The patient P assumes a position wherein the region to be treated is located above the opening 12 of the bed plate 2.

A coarse locating is subsequently undertaken, wherein the source 9 remains in its standby position. For coarse locating, the patient P is first irradiated with the x-ray locating means in the first irradiation direction (angle α1 between the central ray ZS and vertical). The carrier 8 is adjusted in the directions of the x-axis and the y-axis such that the image of the region to be treated coincides with a mark in the x-ray image displayed on a monitor, this mark corresponding in a known way with the projection of the isocenter IZ into the image plane of the x-ray image. When the carrier 8 is aligned in the described way, the region to be treated lies on the central ray ZS proceeding in the direction corresponding to the first irradiation direction.

The C-arm 16 is now pivoted to permit the patient P to be irradiated from the second irradiation direction (angle α2 between the central ray and vertical). The patient P is now irradiated again and the image of the region to be treated is brought into coincidence with the mark in the x-ray image displayed on the monitor with a synchronous drive of the motors for the bed plate 2 in the direction of the z-axis and the carrier 8 in the direction of the x-axis ensuing in the way set forth above. The relative motion between the isocenter IZ and the region to be treated thus ensues in u-direction.

The preliminary locating is thus completed. The region to be treated is located in the isocenter IZ. The source 9 is now moved from its standby position into its working position wherein the coupling cushion 13 presses against the body surface of the patient P. The slight dislocation of the region to be treated from the isocenter IZ, and thus from the focus F of the source 9, which may possibly occur as a result thereof is corrected by a fine locating procedure.

To this end, the x-ray locating means is activated again in the second irradiation direction and the image of the region to be treated is again brought into coincidence with the mark, by adjusting the region to be treated, and the isocenter IZ and the focus F, relative to one another in the u-direction as necessary. The central ray ZS proceeding in the second direction then proceeds through the region to be treated. The C-arm 16 is now adjusted to bring about the first irradiation direction again, the useful x-ray beam proceeding through the opening 10 of the source 9 therein since the source 9 is in its working position. As necessary, the image of the region to be treated is brought into coincidence with the mark by means of a synchronous drive of the motors for the bed plate 2 in the direction of the z-axis and of the carrying part 8 in the direction of the x-axis. Such synchronous drive results in a relative motion between the region to be treated, and the isocenter IZ and the focus F, in the v-direction. The region to be treated is now located in the focus F with the source 9 applied to the patient P.

Figure 4:
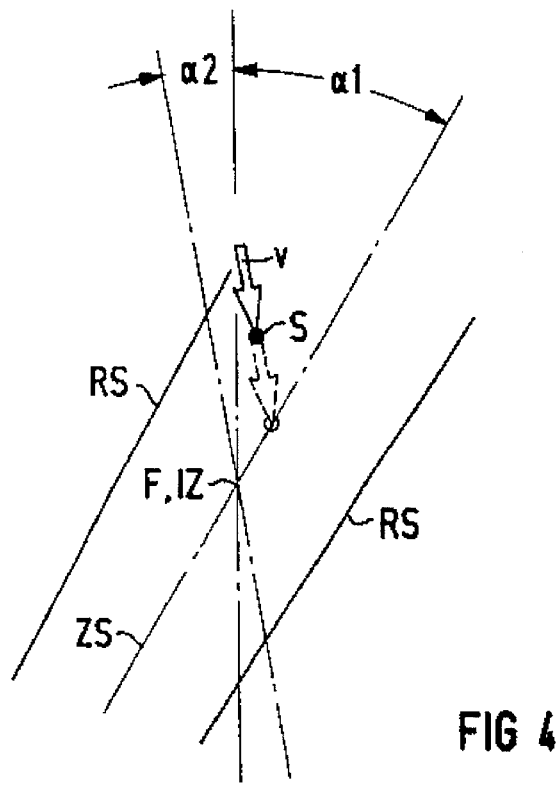
FIGS. 4 and 5 are schematic illustrations respectively illustrating apparatus movements for the operating conditions of FIGS. 2 and 3.
Figure 5:
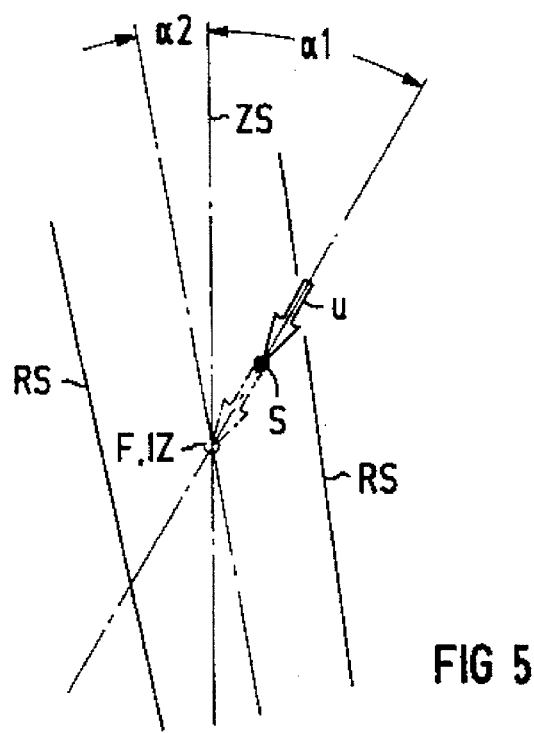

The fine locating procedure is shown again in FIG. 4 and 5. FIG. 4 shows how a region to be treated, for example the stone S of a kidney, is brought into a position for the first irradiation direction such that it lies on the central ray ZS proceeding in the first direction (angle α1), on the basis of motion in the v-direction, parallel to the second direction (angle α2) of the central ray ZS. For the second irradiation direction, FIG. 5 shows how the kidney stone S is positioned on the central ray ZS proceeding in the second direction (angle α2) and thus in the isocenter IZ on the basis of a motion in the u-direction parallel to the first direction (angle α1) of the central ray ZS.

After the region to be treated and the isocenter IZ, which corresponds to the position of the focus F of the acoustic waves, have been brought into coincidence in the described way, charging the region to be treated with the acoustic waves can ensue.

The support table 1, the carriage 7 and the carrier 8 that carries the source 9 and x-ray locating means 14 interact to form a positioning apparatus with which the region to be treated and the focus F are adjustable relative to one another such that the focus F is located in the region to be treated. The drives allocated to the support table 1, to the carriage 7 and to the carrier 8 for adjustment in the z-direction, in the y-direction and in the x-direction from adjustment means with which the region to be treated and the focus F are adjustable relative to one another (1) in a first adjustment direction, namely the y-direction, which intersects the plane between containing the central ray ZS of the x-ray locating means for both irradiation directions, in a second adjustment direction contained in the aforementioned plane and (3) in a third adjustment direction (such as the z-direction) different from the second adjustment direction (such as the x-direction). The adjustment means can thereby be synchronously actuated with respect to the second and third adjustment directions, (such as the x-direction and the z-direction) such that, as disclosed, a relative motion occurs between the region to be treated and the focus F. The region to be treated moves in the direction u proceeding parallel to the first direction of the central ray ZS defined by α1. The focus F moves the direction v proceeding parallel to the direction of the central ray ZS defined by α2. In this way, it is possible to quickly locate a region to be treated and to position it in the way required for the treatment even though neither the first nor the second direction α1 or α2 of the central ray ZS coincides with one of the adjustment directions, namely the x-direction, the y-direction or the z-direction.

As mentioned, the source 9 can be a focused shockwave source. With such a shockwave source, bone conditions can be treated in addition to stone conditions. However, a pressure pulse source as disclosed, for example, in German Utility Model 91 09 025 can alternatively be provided as source 9. Such a source generates negative pressure pulses and is particularly suitable for the treatment of tumors. Further, a therapeutic ultrasound source which emits therapeutic ultrasound as continuous sound for the treatment of tumors can be provided as the source 9. Sources as disclosed in U.S. Pat. No. 4,926,857 and 4,976,255 which unite a pressure pulse source and therapeutic ultrasound source can also be provided as the source 9, for example for treating tumors.

Regardless of the source 9 which is employed, there is the possibility of integrating an ultrasound locating unit therein in a known way, which can be formed in a known way either by an ultrasound B-scanner or by an ultrasound echo locating means (A-Scan). In the case of an ultrasound B-scanner, there is the possibility of introducing it into the opening 19 of the source 9 for the implementation of the ultrasound locating.

Figure 6:
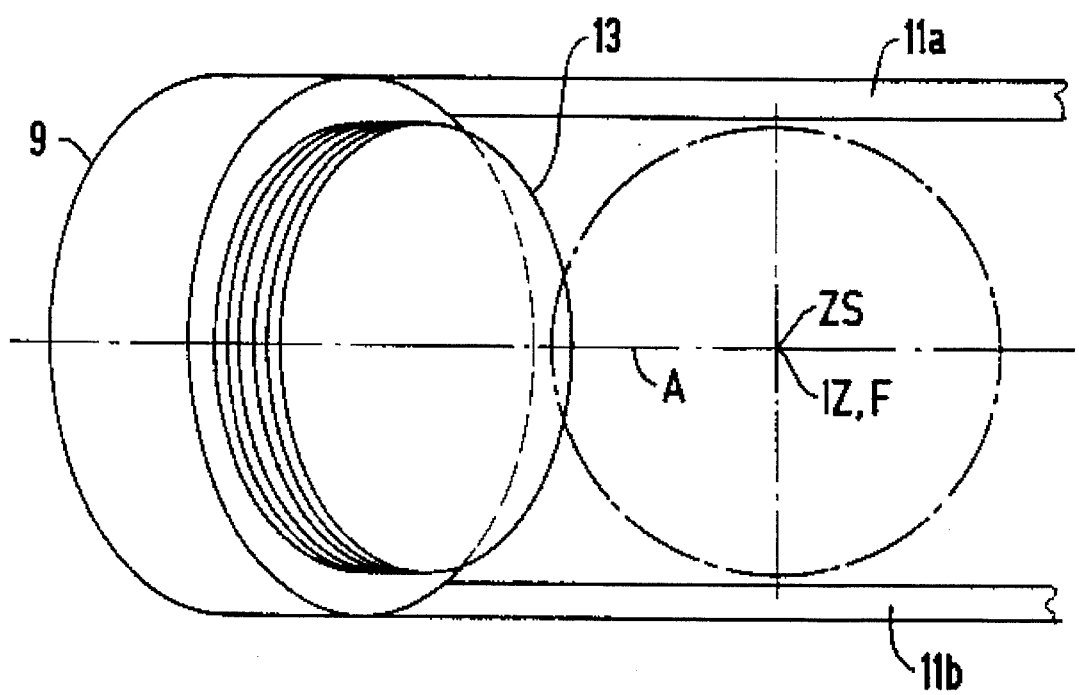
FIG. 6 is a detailed view of the lithotripsy work station according to FIGS. 1 through 3.

As may be seen from FIG. 6, the source carrier 11 has two arms. Its arms 11a and 11b are located outside the useful x-ray beam of the x-ray locating means—the cross-section thereof being indicated with shading in FIG. 6—both in the working position of the source 9 shown in FIG. 6 and the standby position which is indicated with broken lines in FIG. 2. The useful x-ray beam thereby passes between the arms 11a and 11b when the source 9 is in its working position.

The therapy apparatus of the invention has the advantage that the x-ray locating means can be adjusted from its first into its second irradiation direction independently of the source. The relative motions between source and patient are thereby limited to those relative motions that are in fact required in order to bring the region to be treated—potentially after carrying out a preliminary positioning—into the isocenter or into the focus of the source. Dislocations of the patient relative to the source that are caused by the change of irradiation direction thus do not occur.

It is not necessary during the locating procedure to constantly transilluminate the patient with the x-ray locating means. On the contrary, the locating procedure can ensue in a known way largely on the basis of stored x-ray images, what are referred to as "stored shots".

In the exemplary embodiment that has been set forth, the central ray of the x-ray locating means does not proceed parallel to one of the adjustment directions, (x-, y-, and z-directions), in either the first or in the second irradiation direction.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy apparatus for treating a region in a subject with focused acoustic waves comprising:

acoustic waves source means for generating acoustic waves focused to a focus, said acoustic waves source means having an x-ray transparent region;

x-ray locating means for locating a region to be treated in a subject by irradiating said subject from first and second irradiation directions with an x-ray locating beam having a central ray, said central ray assuming a first ray direction for said first irradiation direction and a second ray direction for said second irradiation direction, said first and second ray directions being in a common plane; and positioning means for adjusting said subject and said focus relative to each other for bringing said region to be treated and said focus into coincidence, said positioning means including adjustment means for moving said region to be treated and said focus relative to each other in a first adjustment direction which intersects said plane, and for moving said region to be treated and said focus relative to each other in a second adjustment direction and in a third adjustment direction for producing relative movements between said region to be treated and said focus in each of said second and third adjustment directions for producing a resultant relative motion between said region to be treated and said focus, for said first irradiation direction, which proceeds parallel to the second ray direction for said second irradiation direction for causing said x-ray locating beam to pass through said x-ray transparent region of said acoustic wave source means in said first irradiation direction and to pass by said acoustic waves source means in said second irradiation direction.

2. A therapy apparatus as claimed in claim 1 wherein said adjustment means comprises means for moving said region to be treated and said focus relative to each other in a first adjustment direction which intersects said plane, and for synchronously moving said region to be treated and said focus relative to each other in second and third adjustment directions for producing a resultant relative motion between said region to be treated and said focus, for said first irradiation direction, which proceeds parallel to the second ray direction, and for said second irradiation direction, which proceeds parallel to said first ray direction.

3. A therapy apparatus as claimed in claim 1 wherein said positioning means includes means for adjusting said x-ray locating means and said acoustic waves source means in common in said first and second adjustment directions.

4. A therapy apparatus as claimed in claim 1 wherein said positioning means includes a support table for said subject, and wherein said adjustment means includes means for adjusting said support table in said third adjustment direction.

5. A therapy apparatus as claimed in claim 4 wherein said means for adjusting said support table in said third adjustment direction adjusts said support table vertically.

6. A therapy apparatus as claimed in claim 1 further comprising means for moving said acoustic waves source means to a standby position wherein said acoustic waves source means is disposed outside of said locating beam.

7. A therapy apparatus as claimed in claim 1 wherein said positioning means includes a support table for said patient, said support table having a longitudinal axis, and wherein said plane is disposed substantially at a right angle relative to said longitudinal axis.

8. A therapy apparatus as claimed in claim 1 wherein said positioning means includes a support table for said subject, said support table having a longitudinal axis, and further comprising means for pivoting said x-ray locating means around an axis proceeding substantially parallel to said longitudinal axis.

9. A therapy apparatus as claimed in claim 8 wherein said x-ray locating means comprises an x-ray source and a radiation receiver mounted on a C-arm having a center axis, said center axis forming said axis proceeding substantially parallel to said longitudinal axis.

10. A therapy apparatus as claimed in claim 8 wherein said positioning means comprises means for adjusting said subject and said focus relative to each other for bringing said region to be treated and said focus into coincidence at an isocenter, and wherein said axis of said x-ray locating means proceeding substantially parallel to said longitudinal axis proceeds through said isocenter.

11. A therapy apparatus as claimed in claim 10 wherein said first ray direction and said second ray direction of said x-ray locating means both proceed through said isocenter.

12. A therapy apparatus as claimed in claim 1 wherein said positioning means includes a support table for said subject, said support table having a longitudinal axis, and further comprising means for pivoting said x-ray locating means around an axis coinciding with said longitudinal axis.

13. A therapy apparatus as claimed in claim 12 wherein said x-ray locating means comprises an x-ray source and a radiation receiver mounted on a C-arm having a center axis, said center axis forming said axis coinciding with said longitudinal axis.

14. A therapy apparatus as claimed in claim 12 wherein said positioning means comprises means for adjusting said subject and said focus relative to each other for bringing said region to be treated and said focus into coincidence at an isocenter, and wherein said axis of said x-ray locating means coinciding with said longitudinal axis proceeds through said isocenter.

15. A therapy apparatus as claimed in claim 14 wherein said first ray direction and said second ray direction of said x-ray locating means both proceed through said isocenter.

16. A therapy apparatus as claimed in claim 1 wherein said x-ray locating means comprises an x-ray source and a radiation receiver mounted on a C-arm, and means for pivoting said C-arm around said center axis, wherein said positioning means includes a support table for said subject having a longitudinal axis proceeding substantially parallel to said center axis, wherein said positioning means comprises means for adjusting said subject and said focus relative to each other for bringing said region to be treated and said focus into coincidence at an isocenter, said center axis and said first and second ray directions proceeding through said isocenter, and wherein said plane is disposed at substantially a right angle relative to said longitudinal axis.

17. A therapy apparatus as claimed in claim 1 wherein said x-ray locating means comprises an x-ray source and a radiation receiver mounted on a C-arm, and means for pivoting said C-arm around said center axis, wherein said positioning means includes a support table for said subject having a longitudinal axis coinciding with said center axis, wherein said positioning means comprises means for adjusting said subject and said focus relative to each other for bringing said region to be treated and said focus into coincidence at an isocenter, said center axis and said first and second ray directions proceeding through said isocenter, and wherein said plane is disposed at substantially a right angle relative to said longitudinal axis.

* * * * *